United States Patent
Sugimura et al.

(10) Patent No.: US 10,392,334 B2
(45) Date of Patent: Aug. 27, 2019

(54) METHOD FOR PRODUCING KETONE AND/OR ALCOHOL, AND SYSTEM THEREOF

(71) Applicant: UBE INDUSTRIES, LTD., Ube-shi (JP)

(72) Inventors: Yoshinori Sugimura, Ube (JP); Kazunori Kurosawa, Ube (JP); Kazuo Yamato, Ube (JP); Junichi Kugimoto, Ube (JP); Joji Kawai, Bangkok (TH); Wanna Sirisuksukon, Bangkok (TH); Nantariya Ngamsup, Bangkok (TH)

(73) Assignee: UBE INDUSTRIES, LTD., Ube-Shi (JP)

( * ) Notice: Subject to any disclaimer, the term of this patent is extended or adjusted under 35 U.S.C. 154(b) by 0 days.

(21) Appl. No.: 15/781,055

(22) PCT Filed: Dec. 6, 2016

(86) PCT No.: PCT/JP2016/086217
§ 371 (c)(1),
(2) Date: Jun. 1, 2018

(87) PCT Pub. No.: WO2017/099072
PCT Pub. Date: Jun. 15, 2017

(65) Prior Publication Data
US 2018/0346399 A1 Dec. 6, 2018

(30) Foreign Application Priority Data
Dec. 7, 2015 (JP) .................. 2015-238274

(51) Int. Cl.
| | |
|---|---|
| C07C 45/53 | (2006.01) |
| C07C 35/08 | (2006.01) |
| C07C 49/403 | (2006.01) |
| C07C 27/00 | (2006.01) |
| C07C 29/00 | (2006.01) |
| C07C 27/12 | (2006.01) |
| C07C 29/54 | (2006.01) |

(52) U.S. Cl.
CPC ............. *C07C 45/53* (2013.01); *C07C 27/00* (2013.01); *C07C 27/12* (2013.01); *C07C 29/00* (2013.01); *C07C 29/54* (2013.01); *C07C 35/08* (2013.01); *C07C 49/403* (2013.01)

(58) Field of Classification Search
CPC .......... C07C 45/53; C07C 35/08; C07C 29/54
See application file for complete search history.

(56) References Cited

U.S. PATENT DOCUMENTS

| | | | |
|---|---|---|---|
| 4,238,415 | A | 12/1980 | Bryan |
| 5,905,173 | A | 5/1999 | Kragten et al. |
| 2009/0018367 | A1 | 1/2009 | Wyatt |
| 2009/0054692 | A1 | 2/2009 | Wyatt |

FOREIGN PATENT DOCUMENTS

| | | |
|---|---|---|
| CN | 1397538 A | 2/2003 |
| EP | 0004105 A1 | 9/1979 |
| JP | S53-059650 A | 5/1978 |
| JP | S54-135748 A | 10/1979 |
| JP | S58-192839 A | 11/1983 |
| JP | H9-194408 A | 7/1997 |
| JP | 2004-059515 A | 2/2004 |
| JP | 2005-528455 A | 9/2005 |
| JP | 2008-528528 A | 7/2008 |
| JP | 2008-528537 A | 7/2008 |
| WO | WO 2003/104169 A2 | 12/2003 |
| WO | WO 2013/083512 A1 | 6/2013 |
| WO | WO 2013/083513 A1 | 6/2013 |
| WO | WO 2015/010928 A1 | 1/2015 |

OTHER PUBLICATIONS

International Preliminary Report on Patentability in International Applicatnion No. PCT/JP2016/086217, dated Jul. 12, 2018.
Extended European Search Report dated Jun. 24, 2019 in related European Application No. 16872970.5.

*Primary Examiner* — Sikarl A Witherspoon
(74) *Attorney, Agent, or Firm* — Knobbe, Martens, Olson & Bear LLP

(57) ABSTRACT

A method and a system for inexpensively producing a corresponding target ketone and/or alcohol by decomposing hydroperoxide rapidly and with high selectivity using an aqueous alkaline solution and by recovering and recycling alkali. The method includes neutralizing at least a part of a carboxylic acid in the oxidation reaction solution by contacting the oxidation reaction solution with a first alkaline solution including a carbonate of an alkali metal, and separating the reaction mixture into a first oil phase and a first water phase; decomposing the hydroperoxide and the ester compound in the first oil phase by contacting the first oil phase with a second alkaline solution having a higher pH value than the first alkaline solution, and separating the reaction mixture into a second oil phase and a second water phase; and recovering the carbonate of an alkali metal from the first water phase and recycling the carbonate of an alkali metal to the first alkaline solution.

7 Claims, No Drawings

METHOD FOR PRODUCING KETONE AND/OR ALCOHOL, AND SYSTEM THEREOF

This application is the U.S. National Phase under 35 U.S.C. § 371 of International Application No. PCT/JP2016/086217, filed Dec. 6, 2016, designating the U.S., and published in Japanese as WO 2017/099072 on Jun. 15, 2017, which claims priority to Japanese Patent Application No. 2015-238274, filed Dec. 7, 2015, the entire contents of which are incorporated herein by reference.

TECHNICAL FIELD

The present invention relates to a method for producing ketone and/or alcohol by oxidizing a hydrocarbon compound with molecular oxygen, wherein a hydroperoxide produced as an intermediate is decomposed to produce the ketone and/or alcohol, and relates to a system thereof.

BACKGROUND ART

Oxidization of hydrocarbon compounds with molecular oxygen, and particularly oxidation with air have been examined for many years, and many methods have been disclosed. In the autoxidation of hydrocarbon compounds, the oxidation of cyclohexane is particularly important from an industrial perspective. The obtained cyclohexanone and cyclohexanol are very important compounds as raw materials for nylon 6 and nylon 6,6.

The oxidation of hydrocarbon compounds with molecular oxygen progresses via the corresponding hydroperoxide. The selectivity of an oxidation reaction from a hydrocarbon compound to a hydroperoxide is high, but when hydroperoxides decompose, various byproducts are generated, and therefore the selectivity decreases. In order to prevent this decrease in selectivity, a method is generally adopted in which the oxidation reaction is ended at a stage in which the conversion is low, and the hydroperoxides in the reaction solution that remain without decomposing are decomposed at the next step to produce a ketone and/or alcohol.

Methods for decomposing hydroperoxides can be broadly categorized into two types of methods. One is a method in which a small amount of a transition metal compound or the like is added to decompose the hydroperoxide, and the other is a method in which a hydroperoxide is contacted with an alkaline aqueous solution to decompose the hydroperoxide. Among these, with the former type of method, the rate of decomposition of the hydroperoxide is slow, and the decomposition selectivity is also not very high, and therefore ordinarily the latter type of method is adopted. Note that with the process of the latter type of method, the neutralization of carboxylic acid produced as a byproduct by the oxidation reaction, and the hydrolysis of esters produced as byproducts are simultaneously performed, and therefore this is known as a saponification step.

In the saponification step, in order to decompose a hydroperoxide with high selectivity, it is crucial that hydroperoxide is moved rapidly to the alkaline water phase. This is because radical decomposition of hydroperoxides having low selectivity progresses in the oil phase, and the decomposition selectivity decreases. With the saponification step, in order that hydroperoxides are dissociated and rapidly moved to the water phase, a strong alkaline aqueous solution such as alkali metal hydroxides or the like is used. However, the carboxylic acids generated in the oxidizing step reduce the pH of the saponification step. In order to prevent this, a method is widely adopted in which the saponification step is divided into two steps: a carboxylic acid neutralization step and a hydroperoxide decomposition step, and the oxidation reaction solution and the alkaline aqueous solution are brought into counter-flow-contact. This is called a two-step saponification process. However, the alkaline water phase that is discharged from the carboxylic acid neutralization step has a low pH value, and therefore this cannot be recirculated and used. It is also difficult to recycle and reuse the strong alkali. That is, the two-step saponification process is excellent in hydroperoxide decomposition selectivity, but it is a process with high alkali consumption.

CITATION LIST

Patent Documents

Patent Document 1: Japanese Patent Laid-Open No. S58 (1983)-192839
Patent Document 2: Japanese Patent Laid-Open No. S53 (1978)-59650
Patent Document 3: Japanese Patent Laid-Open No. H9 (1997)-194408
Patent Document 4: Japanese Patent Laid-Open No. 2005-528455
Patent Document 5: Japanese Patent Laid-Open No. 2004-59515
Patent Document 6: Japanese Patent Laid-Open No. 2008-528537
Patent Document 7: WO 2013/083512
Patent Document 8: WO 2013/083513

SUMMARY OF INVENTION

Technical Problem

An object of the present invention is to provide a method to rapidly and highly selectively decompose a hydroperoxide using an alkaline aqueous solution for inexpensively producing a corresponding target ketone and/or alcohol by recovering and recycling the alkali, and to provide a system thereof.

Solution to Problem

The present invention relates to the following matters.
1. A method for producing a ketone and/or alcohol by decomposing a hydroperoxide and an ester compound in an oxidation reaction solution obtained from oxidizing a hydrocarbon compound with molecular oxygen, in which the ketone and/or alcohol has the same number of carbon atoms as the hydrocarbon compound; wherein the method comprising:

a neutralization step for neutralizing at least a part of a carboxylic acid in the oxidation reaction solution by contacting the oxidation reaction solution with a first alkaline solution comprising a carbonate of an alkali metal, and separating the reaction mixture into a first oil phase and a first water phase;

a saponification step for decomposing the hydroperoxide and the ester compound in the first oil phase by contacting the first oil phase with a second alkaline solution having a higher pH value than the first alkaline solution, and separating the reaction mixture into a second oil phase and a second water phase;

an unreacted hydrocarbon recovery step for recovering at least a part of an unreacted hydrocarbon from the second oil phase;

a purification step for obtaining the ketone and/or alcohol from the second oil phase after recovering at least a part of the unreacted hydrocarbon by purification; and an alkali recovery step for recovering the carbonate of an alkali metal from the first water phase and recycling the carbonate of an alkali metal to the first alkaline solution.

2. The method according to item 1, wherein the pH of the first water phase is 8.5 or more and 12.0 or less and the pH of the second water phase is equal to or more than pKa of the hydroperoxide and 14.0 or less.

3. The method according to item 1 or 2, wherein the pH of the second water phase is 12.6 or more and 14.0 or less.

4. The method according to any one of items 1 to 3, wherein the pH of the second water phase is 13.0 or more and 14.0 or less.

5. The method according to any one of items 1 to 4, further comprising a step for recycling a part or all of the second water phase as a part of the first alkaline solution.

6. The method according to any one of items 1 to 5, further comprising a step for recycling a part or all of the second water phase as a part of the second alkaline solution.

7. The method according to any one of items 1 to 6, wherein a transition metal compound is added to the second alkaline solution.

8. The method according to any one of items 1 to 7, wherein the hydrocarbon compound is cyclohexane, the hydroperoxide is cyclohexyl hydroperoxide, the ketone is cyclohexanone, and the alcohol is cyclohexanol.

9. A system for producing a ketone and/or alcohol by decomposing a hydroperoxide and an ester compound in an oxidation reaction solution obtained from oxidizing the hydrocarbon compound with molecular oxygen, in which the ketone and/or alcohol has the same number of carbon atoms as the hydrocarbon compound; wherein the system comprising:

a neutralization unit for neutralizing at least a part of a carboxylic acid in the oxidation reaction solution by contacting the oxidation reaction solution with a first alkaline solution comprising a carbonate of an alkali metal, and separating the reaction mixture into a first oil phase and a first water phase;

a saponification unit for decomposing the hydroperoxide and the ester compound in the first oil phase by contacting the first oil phase with a second alkaline solution having a higher pH value than the first alkaline solution, and separating the reaction mixture into a second oil phase and a second water phase;

an unreacted hydrocarbon recovery unit for recovering at least a part of an unreacted hydrocarbon from the second oil phase;

a purification unit for obtaining the ketone and/or alcohol from the second oil phase after recovering at least a part of the unreacted hydrocarbon by purification;

an alkali recovery unit for recovering the carbonate of an alkali metal from the first water phase and recycling the carbonate of an alkali metal to the first alkaline solution.

Advantageous Effect of Invention

According to the present invention, a hydroperoxide obtained from oxidizing a hydrocarbon compound with molecular oxygen can be rapidly and highly selectively decomposed to produce a target ketone and/or alcohol. Also according to the present invention, a carbonate of an alkali metal can be recovered and recycled at a high yield, and therefore a method for inexpensively producing a target ketone and/or alcohol can be provided. In particular, according to the present invention, a method for inexpensively producing ketones can be provided.

DESCRIPTION OF EMBODIMENTS

The present invention is described in detail as follows.

A hydroperoxide of the present invention is not particularly limited as long as it is the hydroperoxide of a hydrocarbon compound such as a open-chain hydrocarbon, an alicyclic hydrocarbon, or the like. Furthermore, the hydrocarbon compound may have a substituent. Examples include hydroperoxides of hydrocarbon compounds having from 5 to 20 carbon atoms such as cyclopentane, cyclohexane, cycloheptane, cyclooctane, cyclononane, cyclodecane, cyclododecane, cyclopentadecane, cyclohexadecane, and the like. Moreover, a mixture of hydroperoxides obtained by co-oxidizing two or more types of hydrocarbon compounds may also be used. For example, from cyclododecyl hydroperoxide and cyclohexyl hydroperoxide obtained by oxidizing a cyclohexane solution of cyclododecane, laurolactam and caprolactam can be coproduced, which are the raw materials of nylon 12 and nylon 6 ultimately.

Hydroperoxide can be produced by subjecting a corresponding hydrocarbon compound to an oxidation reaction using molecular oxygen without a solvent or in the presence of a solvent. For example, cycloalkyl hydroperoxide can be obtained by subjecting cycloalkane to a liquid phase contact reaction with molecular oxygen such as air, under condition that a reaction temperature is 120 to 180° C. and a reaction pressure is 1 to 20 atm.

As the solvent, the raw material hydrocarbon compound, or benzene, toluene, or the like can be used. In the present invention, the oxidation reaction solution can be used as is, or can be concentrated and used.

The oxidation reaction of the hydrocarbon compound with molecular oxygen is generally performed at a low conversion.

The reaction thereof is limited to a low conversion in order to prevent the successive oxidation of the ketones and alcohol, which are more easily oxidized than the hydrocarbon compound starting material, and to prevent the production of byproducts of higher-order oxides such as carboxylic acid.

A method in which an oxidation reaction is carried out without adding transition metal compound such as cobalt or other ordinarily used as an oxidation catalyst (referred to as uncatalytic oxidation method), and a method in which decomposition of the hydroperoxide in the oxidizing step is suppressed by adding a hydroperoxide stabilizer such as phosphoric acid diester (for example, Japanese Patent Laid-open No. S62 (1987)-120359) and then in the next step (hydroperoxide decomposition step), decomposing the hydroperoxide in a non-oxidizing atmosphere are adopted.

Furthermore, in order to prevent decomposition of the hydroperoxide by stainless steel, which is the material of the reaction vessel, a method for deactivating the surface of the reaction vessel with pyrophosphoric acid salt or the like, and furthermore, a method for coating the oxidation reaction apparatus with PFA (tetrafluoroethylene-perfluoro alkylvinyl ether copolymer) (for example, WO 2011/054809) may be used.

Decomposition of the hydroperoxide is performed under a non-oxidizing atmosphere, but radical decomposition progresses in the oil phase. Radical decomposition is meager in terms of selectivity, and the decomposition selectivity of hydroperoxide is not high.

Moreover, the ketone that is the target substance is present at a relatively high concentration in the oil phase, and therefore oxidation of the ketone by hydroperoxide progresses, and higher order oxides are produced as byproducts from the ketone, and as a result, the hydroperoxide decomposition selectivity decreases further.

In other words, in order to decompose the hydroperoxide with high selectivity, the hydroperoxide must be selectively and rapidly moved to the alkaline water phase, and ionically decomposed in the alkaline water phase.

However, the oil-water distribution equilibrium constant RD of hydroperoxide ([hydroperoxide concentration in the oil phase]/[hydroperoxide concentration in the water phase]) is large, and the hydroperoxide is difficult to distribute in the water phase.

On the other hand, the hydrogen atom of ROO—H of hydroperoxide has an acidic property, and the acid dissociation constant ($K_a$) thereof is from $10^{-12}$ to $10^{-13}$. That is to say, in an alkaline aqueous solution having a pH of 13 or higher, hydroperoxide dissociates into the anion (ROO—) thereof. Therefore, in the abovementioned pH range, the distribution ratio D ([hydroperoxide concentration in the oil phase]/[hydroperoxide+hydroperoxy anion concentration in the water phase]) decreases, and the hydroperoxide concentration in the oil phase decreases.

Furthermore, in an alkaline aqueous solution with a pH of 13 or higher, hydroperoxy anions rapidly decompose into the corresponding ketone and/or alcohol.

In order to replenish the decomposed hydroperoxy anions (to maintain the distribution ratio D of the oil phase and water phase at a constant level), the hydroperoxide in the oil phase rapidly moves into the alkaline water phase. Accordingly, the overall general decomposition rate of the hydroperoxide (rate of the entire process of substance movement, dissociation, and decomposition) accelerates remarkably. In other words, the hydroperoxide can be rapidly decomposed by bringing into contact with a strong alkali having a pH of 13 or higher. As the strong alkaline aqueous solution having a pH of 13 or higher, an aqueous solution comprising alkali metal hydroxide is used.

The RD values of the hydrocarbon compound and the corresponding ketone and alcohol are generally large, and the concentrations of these in the alkaline water phase are low. Accordingly, byproducts produced by oxidizing these compounds with the hydroperoxide are minimal, and the hydroperoxide decomposition selectivity is high.

However, carboxylic acid and carboxylic acid esters produced as byproducts are present in the oxidation reaction solution, and alkali is consumed to neutralize and hydrolyze (saponify) these substances. Above all, the neutralization reaction of carboxylic acid proceeds at a significantly faster pace than the hydroperoxide decomposition reaction, and therefore the pH of the alkali metal hydroxide aqueous solution immediately decreases at the moment when the oxidation reaction solution and the alkali metal hydroxide aqueous solution are contacted. Accordingly, large amounts of alkali metal hydroxides are necessary to maintain a high pH at the time of the hydroperoxide decomposition reaction. In order to decompose hydroperoxide while maintaining a high pH with as little an amount of alkali metal hydroxides as possible, it is necessary that before decomposing the hydroperoxide, a carboxylic acid and carboxylic acid ester, particularly a carboxylic acid, which are by-produced in the oxidation reaction solution, are discharged and removed. This is a neutralization step.

The neutralization step mainly aims at removing the carboxylic acid, and therefore, it is favorable to carry out the neutralization step at a relatively low temperature and at a relatively low pH value. The neutralization step is carried out, for example, at a temperature of 60° C. or more and 140° C. or less, and preferably 80° C. or more and 110° C. or less. The neutralization reaction itself may be carried out at a lower temperature, but as described above, the oxidation of the hydrocarbon compound is carried out at a relatively high temperature, and therefore, when the neutralization reaction is carried out at a temperature of 60° C. or less, cooling is required in order to lower the temperature. Moreover, for the later-described recovery of the unreacted hydrocarbon, reheating is required to cause a relatively large energy loss. On the other hand, when the neutralization reaction is carried out at a temperature of 140° C. or more, the decomposition of the hydroperoxide at a low pH proceeds, and there is a possibility that the decomposition selectivity will decrease.

As a method for lowering the temperature of the oxidation reaction solution to the abovementioned prescribed temperature, a heat exchange with a low-temperature medium may be performed by using a heat exchanger or the like, but as a preferable aspect, there is a method of lowering the temperature of the oxidation reaction solution by using the evaporation latent heat by flash distillation and recovery of the unreacted hydrocarbon compound and/or the oxidation reaction solvent.

In the present invention, a first alkaline solution for neutralizing at least a part of the carboxylic acid in the abovementioned oxidation reaction solution contains a carbonate of an alkali metal. The first alkaline solution may be an alkali metal carbonate aqueous solution or may also be an aqueous solution of a mixture composed of an alkali metal carbonate and an alkali metal hydrogen carbonate. The neutralization step includes a step for carrying out the neutralization reaction, and a step for separating the reaction solution into a first oil phase (hereinafter, also referred to as the neutralization solution) and a first water phase (hereinafter, also referred to as the first waste alkaline solution). By using the abovementioned first alkaline solution, the first waste alkaline solution can be easily regulated so as to fall within the later-described pH range. Moreover, the carbonate can be easily recovered from the later-described alkali recovery step and can be reused.

The used amount of the first alkaline solution in the neutralization step is adjusted such that the pH of the first waste alkaline solution is, for example, 8.5 or more and 12.0 or less, and preferably 9 or more and 10.5 or less. If the pH is 8.5 or less, a part of the carboxylic acid is sent as unneutralized to a saponification step, and in some cases, may decrease the pH of the later-described second alkaline solution. On the other hand, if the pH is 12.0 or more, the decomposition of the hydroperoxide is caused, and in some cases in the pH range, the selectivity may decrease in the decomposition.

The mixing time of the neutralization step is not particularly limited; however, because the neutralization reaction proceeds very rapidly, the mixing time may be short as long as the oxidation reaction solution and the first alkaline solution are sufficiently mixed with each other. For example, when a static mixer is used as a mixing apparatus, the mixing time may be one minute or less.

The separation of the neutralization solution and the first waste alkaline solution may be carried out by using an extraction column such as a perforated plate extraction column, rotating disc extraction column, pulsating perforated plate column, or vibration plate column, in a manner integrated with the neutralization step, or alternatively, may be carried out by using a separation dedicated apparatus such as a settler, centrifuge separator, or liquid cyclone. Among these apparatuses, a combination of a static mixer and a settler is the most simple and easy apparatus.

The residence time of the neutralization solution and the first waste alkaline solution in the separation apparatus is preferably short as long as the oil/water separation is completed, and for example, is 1 minute or more and 60 minutes or less, and preferably 1 minute or more and 30 minutes or less. If the residence time is too short, in some cases it is difficult to control the operation, and the separation of the oil phase and the water phase may be insufficient. If the residence time is too long, it is not preferable because a long and large apparatus is required.

The abovementioned neutralization solution is mixed with the second alkaline solution having a higher pH than the first alkaline solution, the hydroperoxide and the ester compound in the neutralization solution are decomposed, and the corresponding ketone and/or alcohol is obtained. In the saponification step, the precursors other than the hydroperoxide and the ester compound such as dialkyl peroxides are also decomposed, and a ketone and/or alcohol is obtained. This step separates the reaction mixture into the second oil phase (hereinafter, also referred to as a saponification liquid) and the second water phase (hereinafter, also referred to as the second waste alkaline solution).

The type, concentration and used amount of the second alkaline solution are preferably adjusted such that the pH of the second waste alkaline solution discharged from the saponification step is, for example, more than or equal to the pKa of the hydroperoxide and 14.0 or less, preferably 12.6 or more and 14.0 or less, and more preferably 13.0 or more and 14.0 or less. As the second alkaline solution, a caustic alkaline aqueous solution, or a caustic alkali-containing mixed alkaline aqueous solution is preferably used. Examples of the caustic alkali include lithium hydroxide, sodium hydroxide, and potassium hydroxide, and sodium hydroxide is preferable from the viewpoint of the cost.

If the pH of the second waste alkaline solution is lower than the pKa of the hydroperoxide, there is a possibility that the dissociation of the hydroperoxide will not proceed, the distribution ratio D will be high, and most of the hydroperoxide will remain in the oil phase. Therefore, the decomposition rate of the hydroperoxide becomes slow, and in some cases, a long and large saponification reaction tank is required for completely decomposing the hydroperoxide. Moreover, the decomposition of the hydroperoxide in the oil phase is low in selectivity, and thus there is a possibility that the selectivity of the ketone and/or alcohol will decrease.

On the other hand, if the pH of the second waste alkaline solution is higher than 14.0, a large amount of a caustic alkali is necessary to maintain the pH. Moreover, there is a possibility that a condensation reaction such as an aldol condensation will proceed, and the selectivity of the ketone will decrease.

The inlet temperature of the saponification step may not be necessarily the same as the temperature of the neutralization step, but ordinarily the temperatures are the same. The outlet temperature of the saponification step increases as compared with the inlet temperature, due to the decomposition heat generation of the hydroperoxide. The outlet temperature differs depending on the type and concentration of the hydroperoxide, and in the case where the hydroperoxide is cyclohexyl hydroperoxide, the outlet temperature is, for example, 80° C. or more and 170° C. or less, and preferably 90° C. or more and 150° C. or less. If the temperature is too low, because the hydrolysis rates of the hydroperoxide and ester are slow, a long and large reaction tank is required for completing these decompositions. On the other hand, if the temperature is too high, there is a possibility that the decomposition selectivity of the hydroperoxide will decrease. Note that if the outlet temperature of the saponification step exceeds the abovementioned temperature due to the heat generation of decomposition of the hydroperoxide, it is preferable that the outlet temperature is controlled so as to fall within the abovementioned temperature range by cooling the saponification apparatus.

The residence time in the saponification step is chosen so as to complete the decomposition of the hydroperoxide. The residence time of the hydroperoxide decomposition step may vary depending on the temperature, pH of the alkali phase, oil/water ratio, oil/water mixing condition, and the like, but a long residence time is not preferable because requiring a long residence time means that a long and large reaction apparatus is necessary. Accordingly, the reaction conditions are set such that the residence time is 2 hours or less, and preferably 1 hour or less. On the other hand, the hydroperoxide decomposition reaction is an exothermic reaction, and therefore it is preferable that a residence time is 1 minute or more for the purpose of controlling the reaction.

The saponification apparatus is not particularly limited, and by using an extraction column such as a perforated plate extraction column, rotating disc extraction column, pulsating perforated plate column, and vibration plate column, the hydroperoxide decomposition reaction and ester hydrolysis reaction, and the second waste alkali separation in the next step may be performed within a single apparatus, or the saponification reaction and the separation may be performed in separate apparatuses. In the case of the latter, for example, a stirring tank type reactor, a tubular type reactor, and a column type reactor are used for the saponification reaction. Inserting a static mixer or the like directly before the reactor for the purpose of mixing and dispersing the oil/water is a preferable aspect. For example, a settler, centrifuge apparatus, liquid cyclone, and the like are used in the separation into the second waste alkali. Among these, a combination of a static mixer, column type reactor, and settler is the most simple and easy apparatus. Moreover, parts which promote separation such as a coalescer may be disposed inside the settler. The temperatures of the outlet of the saponification reaction step and the separating step may be different, but ordinarily the temperatures are the same.

The residence time of the second waste alkali separation step is preferably short as long as the oil/water separation is completed, and for example, it is 1 minute or more and 60 minutes or less, and is preferably 1 minute or more and 30 minutes or less. If the residence time is too short, in some cases controlling the operation is difficult and separating the oil phase and water phase is insufficient. If the residence time is too long, it is not preferable because a long and large apparatus is required.

After the saponification step, from the abovementioned saponification liquid, at least a part of the unreacted hydrocarbon is recovered. Then, the saponification liquid, from which at least a part of the unreacted hydrocarbon has been recovered, is purified to obtain ketone and/or alcohol. In this way, the ketone and/or alcohol is (are) produced.

The recovery method of the unreacted hydrocarbon is not particularly limited, but ordinarily the unreacted hydrocarbon is recovered by distillation. The distillation may be any of flash distillation, pressure distillation, normal-pressure distillation, and reduced pressure distillation, and may also be a combination of these distillation methods. The recovered unreacted hydrocarbon is typically recycled to the oxidation step.

The purification method to obtain the ketone and/or alcohol is not particularly limited, the purification may be performed by adopting crystallization, recrystallization, extraction and the like, but is generally a method in which the purification is performed by distillation. The pressure in the distillation may be any of increased pressure, normal pressure, and reduced pressure, but it is appropriately selected depending on the vapor pressures of the ketone and/or alcohol as the production target substance and the by-product impurities. The order of the distillation is not particularly limited, but when the boiling point of the ketone and the boiling point of the alcohol as main products are compared, generally the alcohol has a higher boiling point, and thus in general, a purification method is performed in the order of the removal of low-boiling-point impurities, the obtaining the target ketone, the obtaining the target alcohol, and the discharge of the high-boiling point impurities. If the unreacted hydrocarbon is contained in the distillation fraction of the low-boiling point impurities, the distillation fraction can also be recycled to the oxidation step. If the production target substance is the ketone, the obtained alcohol is converted into a ketone by a reaction such as dehydrogenation, then recycled to the ketone purification step, and the ketone can be obtained. If the production target substance is the alcohol, the obtained ketone is converted into an alcohol by a reaction such as hydrogenation, and then the alcohol can also be obtained in the alcohol purification step.

In the abovementioned production method, from the first waste alkaline solution, the carbonate of the alkali metal is recovered. Then, the carbonate of the alkali metal is recycled to the first alkaline solution. By the alkali recovery step, the carbonate of the alkali metal can be recovered and recycled at a high yield, and therefore a method for inexpensively producing a target ketone and/or alcohol can be provided.

It is a preferable aspect that a part or all of the second waste alkaline solution is recycled as a part of the first alkaline solution. The object of the aforementioned recycling is the reduction of the used amount of alkali. Accordingly, the recycled amount of the second waste alkaline solution is preferably adjusted such that the pH of the first waste alkaline solution is, for example, 8.5 or more and 12.0 or less, and preferably 9 or more and 10.5 or less.

It is also a preferable aspect that a part or all of the second waste alkaline solution is recycled as a part of the second alkaline solution. The object of the aforementioned recycling is to decrease the oil-water distribution equilibrium constant RD of the hydroperoxide ([hydroperoxide concentration in the oil phase]/[hydroperoxide concentration in the water phase]). In other words, the object of the aforementioned recycling is to increase the decomposition rate of the hydroperoxide by increasing the equilibrium concentration of the hydroperoxide in the alkaline water phase. Moreover, the circulation of the second waste alkaline solution decreases the oil/water interfacial tension and promotes the formation of the oil/water emulsion. Accordingly, the mass transfer of the hydroperoxide between oil and water is promoted, and the decomposition rate of the hydroperoxide is increased.

It is preferable to set the amount ratio of the recycled amount of the second waste alkaline solution and the amount of the second alkaline solution such that the pH of the second waste alkaline solution is more than or equal to the pKa of the hydroperoxide, for example, 12.6 or more. If the pH of the second waste alkaline solution is lower than the aforementioned pH, there is a possibility that the decomposition rate of the hydroperoxide will be insufficient even by taking into consideration the aforementioned decomposition promotion effect of the hydroperoxide. Therefore, there is a possibility that the decomposition selectivity of the hydroperoxide into the ketone and/or alcohol will decrease.

It is a preferable aspect that a transition metal compound is added to the second alkaline solution because the addition of a transition metal compound to the second alkaline solution promotes the decomposition of the hydroperoxide. Moreover, when the object is to obtain a ketone, the aforementioned addition of the transition metal compound is particularly preferable because the production ratio of ketone/alcohol increases. The concentration of the transition metal in the alkaline phase is, for example, 0.1 weight ppm or more and 1000 weight ppm or less, and preferably 1 weight ppm or more and 100 weight ppm or less. If the transition metal concentration is too low, a remarkable decomposition promotion effect of the hydroperoxide is not obtained. If the transition metal concentration is too high, a further decomposition acceleration effect of the hydroperoxide, exceeding a certain limit, is not exhibited, which is not preferable because a transition metal catalyst is only wasted.

However, such a transition metal compound as described above is added to the second alkaline solution, it is necessary to pay attention because the decomposition of the hydroperoxide in the neutralization step is promoted. By combining the temperature decrease (80° C. to 90° C.) and the residence time reduction (1 minute to 10 minutes) in the neutralization step, the decomposition percentage of the hydroperoxide is adjusted to be, for example, 20% or less, and preferably 10% or less.

The first waste alkaline solution is typically mixed with a fuel and combusted in a combustion furnace. All or a part of the second waste alkaline solution is also typically combusted in a combustion furnace. As the fuel, refined fossil fuels such as heavy oil and the like may be used, but organic substance-containing liquid waste such as waste oil and the like may be effectively used. The carboxylic acid salts and the like in the waste alkali is recovered as carbonates of alkali metals, and are dissolved in water to be recycled as the first alkaline solution to the neutralization step. In other words, this process is a process of recovering as carbonates almost all of the alkali metal salts, and at least the alkalis necessary for neutralization are almost all recovered and recycled. Moreover, the redundant alkali metal carbonates can also be used as the alkali source for the second alkaline solution, or can also be used as another alkali source.

If a transition metal is contained in the waste alkaline solution, this is typically recovered as a transition metal oxide. Since the solubility of the oxide of a transition metal in an alkaline aqueous solution is very low, the transition metal oxide may be recycled to the neutralization step as the first alkaline solution that contains the precipitate of the transition metal oxide, but alternatively the transition metal oxide is be once separated from the alkali metal carbonate aqueous solution to be recycled, dissolved once again in a mineral acid or the like and adjusted to an appropriate pH value, and then may be recycled to the saponification step together with the second alkaline solution.

Inserting a waste alkali concentration step before combusting the waste alkaline solution is a preferable aspect because it has the merits of reducing the fuel for combustion in the alkali recovery step and enabling a reduction in the size of the combustion furnace.

The waste alkali is concentrated by distillation, flash distillation and the like, and water is removed. Through concentration, the trace amounts of ketones and/or alcohol dissolved in the waste alkali can also be recovered with distilled water. Furthermore, by reusing the recovered water as water for dissolving the recovered alkali, there is merit in reducing the hydrocarbon-unit-consumption.

As the concentration ratio is increased, the abovementioned effect is more remarkably exhibited, but operational problems such as an increase in the viscosity of the waste alkali concentrated liquid occur, and therefore, for example, operation at a concentration of 1.5 times or more and 10 times or less, and preferably at a concentration of 2 times or more and 5 times or less is favorable.

Next, a system for producing ketone and/or alcohol is described as follows.

The system for producing a ketone and/or alcohol of the present invention is a system for producing a ketone and/or alcohol by decomposing a hydroperoxide and an ester compound in an oxidation reaction solution obtained from oxidizing the hydrocarbon compound with molecular oxygen, in which the ketone and/or alcohol has the same number of carbon atoms as the hydrocarbon compound; wherein the system comprising:

a neutralization unit for neutralizing at least a part of a carboxylic acid in the oxidation reaction solution by contacting the oxidation reaction solution with a first alkaline solution comprising a carbonate of an alkali metal, and separating the reaction mixture into a first oil phase and a first water phase;

a saponification unit for decomposing the hydroperoxide and the ester compound in the first oil phase by contacting the first oil phase with a second alkaline solution having a higher pH value than the first alkaline solution, and separating the reaction mixture into a second oil phase and a second water phase;

an unreacted hydrocarbon recovery unit for recovering at least a part of an unreacted hydrocarbon from the second oil phase;

a purification unit for obtaining the ketone and/or alcohol from the second oil phase after recovering at least a part of the unreacted hydrocarbon by purification;

an alkali recovery unit for recovering the carbonate of an alkali metal from the first water phase and recycling the carbonate of an alkali metal to the first alkaline solution.

(Neutralization Unit)

The neutralization unit includes, for example, a neutralization reaction tank in which the oxidation reaction solution and the first alkaline solution containing the carbonate of an alkali metal are brought into contact. The neutralization unit neutralizes at least a part of the carboxylic acid in the oxidation reaction solution by the abovementioned action, and subsequently separates the reaction mixture into the first oil phase and the first water phase.

(Saponification Unit)

The saponification unit includes, for example, a saponification reaction tank in which the first oil phase and the second alkaline solution having a higher pH value than the first alkaline solution are brought into contact. The saponification unit decomposes the hydroperoxide and the ester compound in the first oil phase by the abovementioned action, and subsequently separates the reaction mixture into the second oil phase and the second water phase.

(Unreacted Hydrocarbon Recovery Unit)

The unreacted hydrocarbon recovery unit includes, for example, a hydrocarbon recovery apparatus which recovers at least a part of the unreacted hydrocarbon from the second oil phase by a method such as distillation.

(Purification Unit)

The purification unit includes, for example, a purification apparatus for obtaining the ketone and/or alcohol, by a method such as distillation, from the second oil phase in which at least a part of the unreacted hydrocarbon has been recovered.

(Alkali Recovery Unit)

The alkali recovery unit includes, for example, a combustion furnace in which the first water phase is combusted, and the carbonate of the alkali metal is recovered. Moreover, the alkali recovery unit is further provided with, for example, a dissolution tank for dissolving the recovered carbonate of the alkali metal into water, and a piping for recycling the resulting aqueous solution to the neutralization unit. Note that the abovementioned recovery may also be performed simultaneously for the second water phase.

Each of the abovementioned units is connected by piping to send the targeted substance sequentially to the next unit.

EXAMPLES

The present invention is described in greater detail below with the presentation of experiments relating to the decomposition of cyclohexyl hydroperoxide (CHP), which is produced by oxidizing cyclohexane (Cx) with molecular oxygen. However, the present invention is not limited to the following examples.

Note that the selectivities in Reference Examples, Examples and Comparative Examples are calculated as follows. For examples, the total selectivity (CxONOL) of cyclohexanone (CxON) and cyclohexanol (CxOL) is determined by analyzing molar quantities of the cyclohexyl hydroperoxide (CHP), cyclohexanone (CxON), cyclohexanol (CxOL) and byproducts by using gas chromatography and a total organic carbon meter (TOC), and by calculating by the following equation. Here, the amount (moles) of solvent consumption is the molar amount obtained by subtracting the total molar amount of the CHP, CxON, CxOL and byproducts (molar amount converted based on carbon number of 6; hereinafter referred to as C-6 converted molar amount) before the reaction from the total molar mount of the CHP, CxON, CxOL, and byproducts after the reaction (molar amount converted to a carbon count of 6). Note that this solvent consumption amount (mol) is equal to the amount (mol) of Cx oxidized by CHP, which corresponds to difference between the molar amount (C-6 converted molar amount) of all products discharged from the saponification step and the molar amount (C-6 converted molar amount) of all products fed to the neutralization step.

CxONOL Selectivity (%)=[Amount of CxON produced (moles)+Amount of CxOL produced (moles)]/[Amount of CHP consumed (moles)+ Amount of solvent consumed (moles)]×100     [Equation 1]

[A Suitable pH for the Neutralization Step and the Saponification Step]

Reference Example 1

Amounts of 450 g of cyclohexane and 40 g of a 17 wt % sodium carbonate aqueous solution were charged into a 1000 mL internal capacity reactor made of SUS having the surface coated with Teflon (registered trademark), and the materials were heated to 140° C. Into this mixed liquid, 50 g of a cyclohexane solution containing 20 wt % of cyclohexyl hydroperoxide, 10 wt % of cyclohexanone, and 20 wt % of cyclohexanol was pressed, and the cyclohexyl hydroperoxide decomposition rate was measured while obtaining samples at each prescribed time. The overall decomposition rate constant of the cyclohexyl hydroperoxide was 0.065 (1/minute), and the decomposition percentage after 20 minutes was 72.7%. Note that the pH of the water phase after the reaction was 11.23.

Reference Example 2

The reaction was carried out under the same conditions as in [Reference Example 1] except that the 17 wt % sodium carbonate aqueous solution was changed to a mixed alkaline aqueous solution composed of 99 wt % of 17 wt % sodium carbonate aqueous solution and 1 wt % of 10 wt % sodium hydroxide aqueous solution. The overall decomposition rate constant of the cyclohexyl hydroperoxide was 0.100 (1/minute), and the decomposition percentage after 20 minutes was 86.5%. Note that the pH of the water phase after the reaction was 11.77.

Reference Example 3

The reaction was carried out under the same conditions as in [Reference Example 1] except that the 17 wt % sodium carbonate aqueous solution was changed to a mixed alkaline aqueous solution composed of 98 wt % of 17 wt % sodium carbonate aqueous solution and 2 wt % of 10 wt % sodium hydroxide aqueous solution. The overall decomposition rate constant of the cyclohexyl hydroperoxide was 0.100 (1/minute), and the decomposition percentage after 20 minutes was 86.6%. Note that the pH of the water phase after the reaction was 12.31.

Reference Example 4

The reaction was carried out under the same conditions as in [Reference Example 1] except that the 17 wt % sodium carbonate aqueous solution was changed to a mixed alkaline aqueous solution composed of 97 wt % of 17 wt % sodium carbonate aqueous solution and 3 wt % of 10 wt % sodium hydroxide aqueous solution. The overall decomposition rate constant of the cyclohexyl hydroperoxide was 0.097 (1/minute), and the decomposition percentage after 20 minutes was 85.6%. Note that the pH of the water phase after the reaction was 12.58.

Reference Example 5

The reaction was carried out under the same conditions as in [Reference Example 1] except that the 17 wt % sodium carbonate aqueous solution was changed to a mixed alkaline aqueous solution composed of 96 wt % of 17 wt % sodium carbonate aqueous solution and 4 wt % of 10 wt % sodium hydroxide aqueous solution. The overall decomposition rate constant of the cyclohexyl hydroperoxide was 0.115 (1/minute), and the decomposition percentage after 20 minutes was 90.0%. Note that the pH of the water phase after the reaction was 12.82.

Reference Example 6

The reaction was carried out under the same conditions as in [Reference Example 1] except that the 17 wt % sodium carbonate aqueous solution was changed to a mixed alkaline aqueous solution composed of 95 wt % of 17 wt % sodium carbonate aqueous solution and 5 wt % of 10 wt % sodium hydroxide aqueous solution. The overall decomposition rate constant of the cyclohexyl hydroperoxide was 0.166 (1/minute), and the decomposition percentage after 20 minutes was 96.4%. Note that the pH of the water phase after the reaction was 12.93.

Reference Example 7

The reaction was carried out under the same conditions as in [Reference Example 1] except that the 17 wt % sodium carbonate aqueous solution was changed to a mixed alkaline aqueous solution composed of 90 wt % of 17 wt % sodium carbonate aqueous solution and 10 wt % of 10 wt % sodium hydroxide aqueous solution. The overall decomposition rate constant of the cyclohexyl hydroperoxide was 0.249 (1/minute), and the decomposition percentage after 20 minutes was 99.3%. Note that the pH of the water phase after the reaction was 13.40.

Reference Example 8

The reaction was carried out under the same conditions as in [Reference Example 1] except that the 17 wt % sodium carbonate aqueous solution was changed to 10 wt % sodium hydroxide aqueous solution. The overall decomposition rate constant of the cyclohexyl hydroperoxide was 1.825 (1/minute), and the decomposition percentage after 20 minutes was 100.0%. Note that the pH of the water phase after the reaction was 13.83.

Reference Example 9

The reaction was carried out in the same manner as in [Reference Example 1] except that the reaction time was changed to 75 minutes. After separating the reaction solution into an oil phase and a water phase, GC analysis of each phase and TOC analysis of the water phase were carried out to calculate selectivities of CxON and CxOL according to the above formula [Equation 1]. The CHP decomposition percentage was 100%, CxON selectivity was 51.7%, the CxOL selectivity was 25.8%, the total selectivity of CxON and CxOL was 77.5%, and the ratio of generated CxON to CxOL (CxON/CxOL) was 2.0. Note that the pH of the water phase after the reaction was 11.10.

Reference Example 10

The reaction was carried out in the same manner as in [Reference Example 2] except that the reaction time was changed to 50 minutes. After separating the reaction solution into an oil phase and a water phase, GC analysis of each phase and TOC analysis of the water phase were carried out to calculate selectivities of CxON and CxOL according to the above formula [Equation 1]. The CHP decomposition percentage was 100%, CxON selectivity was 51.9%, the CxOL selectivity was 25.9%, the total selectivity of CxON and CxOL was 77.8%, and the ratio of generated CxON to CxOL was 2.0. Note that the pH of the water phase after the reaction was 11.72.

Reference Example 11

The reaction was carried out in the same manner as in [Reference Example 3] except that the reaction time was changed to 50 minutes. After separating the reaction solution into an oil phase and a water phase, GC analysis of each phase and TOC analysis of the water phase were carried out to calculate selectivities of CxON and CxOL according to the above formula [Equation 1]. The CHP decomposition percentage was 100%, CxON selectivity was 52.0%, the CxOL selectivity was 26.0%, the total selectivity of CxON and CxOL was 78.0%, and the ratio of generated CxON to CxOL (CxON/CxOL) was 2.0. Note that the pH of the water phase after the reaction was 12.15.

Reference Example 12

The reaction was carried out in the same manner as in [Reference Example 4] except that the reaction time was changed to 50 minutes. After separating the reaction solution into an oil phase and a water phase, GC analysis of each phase and TOC analysis of the water phase were carried out to calculate selectivities of CxON and CxOL according to the above formula [Equation 1]. The CHP decomposition percentage was 100%, CxON selectivity was 52.1%, the CxOL selectivity was 26.0%, the total selectivity of CxON and CxOL was 78.1%, and the ratio of generated CxON to CxOL (CxON/CxOL) was 2.0. Note that the pH of the water phase after the reaction was 12.42.

Reference Example 13

The reaction was carried out in the same manner as in [Reference Example 5] except that the reaction time was changed to 40 minutes. After separating the reaction solution into an oil phase and a water phase, GC analysis of each phase and TOC analysis of the water phase were carried out to calculate selectivities of CxON and CxOL according to the above formula [Equation 1]. The CHP decomposition percentage was 100%, CxON selectivity was 55.4%, the CxOL selectivity was 24.1%, the total selectivity of CxON and CxOL was 79.5%, and the ratio of generated CxON to CxOL (CxON/CxOL) was 2.3. Note that the pH of the water phase after the reaction was 12.69.

Reference Example 14

The reaction was carried out in the same manner as in [Reference Example 6] except that the reaction time was changed to 30 minutes. After separating the reaction solution into an oil phase and a water phase, GC analysis of each phase and TOC analysis of the water phase were carried out to calculate selectivities of CxON and CxOL according to the above formula [Equation 1]. The CHP decomposition percentage was 100%, CxON selectivity was 57.2%, the CxOL selectivity was 22.9%, the total selectivity of CxON and CxOL was 80.1%, and the ratio of generated CxON to CxOL (CxON/CxOL) was 2.5. Note that the pH of the water phase after the reaction was 12.92.

Reference Example 15

The reaction was carried out in the same manner as in [Reference Example 7] except that the reaction time was changed to 20 minutes. After separating the reaction solution into an oil phase and a water phase, GC analysis of each phase and TOC analysis of the water phase were carried out to calculate selectivities of CxON and CxOL according to the above formula [Equation 1]. The CHP decomposition percentage was 100%, CxON selectivity was 64.7%, the CxOL selectivity was 20.2%, the total selectivity of CxON and CxOL was 84.9%, and the ratio of generated CxON to CxOL (CxON/CxOL) was 3.2. Note that the pH of the water phase after the reaction was 13.4.

Reference Example 16

The reaction was carried out in the same manner as in [Reference Example 8] except that the reaction time was changed to 10 minutes. After separating the reaction solution into an oil phase and a water phase, GC analysis of each phase and TOC analysis of the water phase were carried out to calculate selectivities of CxON and CxOL according to the above formula [Equation 1]. The CHP decomposition percentage was 100%, CxON selectivity was 72.8%, the CxOL selectivity was 18.2%, the total selectivity of CxON and CxOL was 91.0%, and the ratio of generated CxON to CxOL (CxON/CxOL) was 4.0. Note that the pH of the water phase after the reaction was 13.82.

[Measurement of pKa of Hydroperoxide]

Reference Example 17

Amounts of 450 g of cyclohexane, 38 g of a 17 wt % sodium carbonate aqueous solution, and 2 g of a 10 wt % sodium hydroxide aqueous solution were charged into a 1000 mL internal capacity reactor made of SUS having the surface coated with Teflon (registered trademark), and stirred sufficiently at 25° C. Into this mixed liquid, 50 g of a cyclohexane solution containing 20 wt % of cyclohexyl hydroperoxide, 10 wt % of cyclohexanone, and 20 wt % of cyclohexanol was added, and the resulting mixture was stirred further for 5 minutes. After allowing the mixture to stand still and to be separated, the CHP concentration in the oil phase was quantitatively determined by gas chromatography, and the CHP concentration in the water phase was quantitatively determined by gas chromatography and iodometry. Moreover, the pH of the water phase was measured, and the hydrogen ion concentration was calculated.

D=[CHP concentration in oil phase (GC analysis)]/ [CHP concentration in water phase (iodometry analysis)]

$K_D$=[CHP concentration in oil phase (GC analysis)]/ [CHP concentration in water phase (GC analysis)]

$pK_a = -\log_{10}\{(K_D/D \cdot 1)[H^+]\}$

From the above-described formula, the pKa was calculated and found to be 12.62.

Reference Example 18

The pKa was calculated by the same method as [Reference Example 17] except that the oil phase of [Reference Example 17] was changed to an oxidation reaction solution in which cyclohexane was oxidized with air and the conversion of cyclohexane was 4.0%, and the water phase was changed to 10 wt % sodium hydroxide aqueous solution. pKa was 12.47. Note that, the oxidation reaction solution of cyclohexane contained 0.89 wt % of CxON, 2.01 wt % of CxOL and 0.98 wt % of CHP, and the AV value and the EV value were respectively 2.69 mgKOH/g and 1.14 mgKOH/g.

The above results are summarized in Table 1 below.

TABLE 1

| | Alkali composition | | reaction time (min) | After reaction pH | CHP Conversion (%) | CHP decomposition rate constant (1/min) | Selectivity (%) | | | |
| --- | --- | --- | --- | --- | --- | --- | --- | --- | --- | --- |
| | 17% Na$_2$CO$_3$ (wt %) | 10% NaOH (wt %) | | | | | CxON | CxOL | CxON + CxOL | CxON/ CxOL |
| Ref-Ex. 1 | 100 | 0 | 20 | 11.23 | 72.7 | 0.065 | — | — | — | — |
| Ref-Ex. 2 | 99 | 1 | 20 | 11.77 | 86.5 | 0.1 | — | — | — | — |
| Ref-Ex. 3 | 98 | 2 | 20 | 12.31 | 86.5 | 0.1 | — | — | — | — |
| Ref-Ex. 4 | 97 | 3 | 20 | 12.58 | 85.6 | 0.097 | — | — | — | — |
| Ref-Ex. 5 | 96 | 4 | 20 | 12.82 | 90.0 | 0.115 | — | — | — | — |
| Ref-Ex. 6 | 95 | 5 | 20 | 12.93 | 96.4 | 0.166 | — | — | — | — |
| Ref-Ex. 7 | 90 | 10 | 20 | 13.4 | 99.3 | 0.249 | — | — | — | — |
| Ref-Ex. 8 | 0 | 100 | 20 | 13.83 | 100.0 | 1.825 | — | — | — | — |
| Ref-Ex. 9 | 100 | 0 | 75 | 11.1 | 100.0 | — | 51.7 | 25.8 | 77.5 | 2.0 |
| Ref-Ex. 10 | 99 | 1 | 50 | 11.72 | 100.0 | — | 51.9 | 25.9 | 77.8 | 2.0 |
| Ref-Ex. 11 | 98 | 2 | 50 | 12.15 | 100.0 | — | 52.0 | 26.0 | 78.0 | 2.0 |
| Ref-Ex. 12 | 97 | 3 | 50 | 12.42 | 100.0 | — | 52.1 | 26.0 | 78.1 | 2.0 |
| Ref-Ex. 13 | 96 | 4 | 40 | 12.69 | 100.0 | — | 55.4 | 24.1 | 79.5 | 2.3 |
| Ref-Ex. 14 | 95 | 5 | 30 | 12.92 | 100.0 | — | 57.2 | 22.9 | 80.1 | 2.5 |
| Ref-Ex. 15 | 90 | 10 | 20 | 13.4 | 100.0 | — | 64.7 | 20.2 | 84.9 | 3.2 |
| Ref-Ex. 16 | 0 | 100 | 10 | 13.82 | 100.0 | — | 72.8 | 18.2 | 91.0 | 4.0 |

Ref-Ex. = Reference Example

As can be seen from the above results, when the pH after the reaction is equal to or more than the pKa of CHP, the overall decomposition rate constant of CHP is increased and the selectivity is particularly improved Example 1

In a 100 mL autoclave (neutralization tank) having an inlet and an outlet, the oxidation reaction solution of [Reference Example 18] and the first alkaline solution composed of a 17 wt % sodium carbonate aqueous solution were fed at the rates of 20.1 g/min and 0.36 g/min, respectively, and the neutralization of the carboxylic acids in the oxidation reaction solution was performed. The temperature of the neutralization step was 120° C., and the discharged liquid was separated in the separation tank. The pH of the first waste alkaline solution discharged after the separation was 9.57. The CHP conversion, which was calculated from the GC analyses of the neutralization solution and the first waste alkaline solution and the TOC analysis of the first waste alkaline solution, was 4.3%, and the selectivities of CxON and CxOL were 51.7% and 25.8%, respectively. The obtained neutralization solution was mixed with the second alkaline solution composed of a 10% sodium hydroxide aqueous solution having a feed rate of 0.136 g/min, and was sent to the saponification reaction tank formed of a 500 mL autoclave. The temperature of the saponification step was 140° C., and the discharged liquid was separated in the separation tank. The pH of the second waste alkaline solution discharged after the separation was 13.89. The CHP conversion calculated from the GC analyses of the saponification liquid, the first waste alkaline solution, and the second waste alkaline solution and the TOC analyses of the first waste alkaline solution and the second waste alkaline solution was 100%, the selectivities of CxON and CxOL were 71.9% and 18.5%, respectively, and the selectivity of CxONOL was 90.4%. The abovementioned continuous reaction operation was performed for 8 hours, the first waste alkaline solution and the second waste alkaline solution were mixed and evaporated to dryness, the dried product was fired in the air at 1000° C. for 30 minutes by using a muffle furnace, and thus 32.3 g of a powder was recovered. From the results of an X-ray diffraction analysis, the powder was identified as anhydrous sodium carbonate, and the powder did not contain sodium hydroxide or sodium oxide. The amount of the sodium carbonate and the amount of the sodium hydroxide consumed by the 8-hour operation were 29.4 g and 6.5 g (both in terms of anhydrates), respectively.

Example 2

The operation was carried out in the same manner as in [Example 1] except that the feed amount of the second alkaline solution was 0.107 g/min. The pH of the second waste alkaline solution was 13.37, the final conversion of CHP was 100%, the final selectivities of CxON and CxOL were respectively 63.5% and 20.4%, and the selectivity of CxONOL was 83.9%. The amount of sodium carbonate consumed was 29.4 g and the amount of sodium hydroxide consumed was 5.2 g, while the amount of sodium carbonate recovered was 30.8 g.

Comparative Example 1

The oxidation reaction solution was fed directly to the saponification step. Further, the feed amount of 10% sodium hydroxide aqueous solution (corresponding to the second alkaline solution) fed to the saponification tank was increased to 0.487 g/min. The pH of the waste alkaline solution (corresponding to the second waste alkaline solution) discharged from the saponification step was 12.32, the final conversion of CHP was 80.7%, the final selectivities of CxON and CxOL were respectively 52.1% and 26.8%, and the CxONOL selectivity was 78.9%. The amount of sodium hydroxide consumed was 23.4 g and the recovered substance was 26.3 g of sodium carbonate. Sodium hydroxide was not recovered.

Example 3

The operation was carried out in the same manner as in [Example 1] except that a mixed solution composed of 0.27 g/min of a 17 wt % sodium carbonate aqueous solution and a second waste alkaline solution (whole amount) recycled from the saponification step was fed as a first alkaline solution to the neutralization step. The pH of the first waste alkaline solution was 9.55, the CHP conversion was 4.1%, and the selectivities of CxON and CxOL were 52.1% and 26.0%, respectively. The pH of the second waste alkali after saponification was 13.88, the CHP conversion was 100%, the final selectivities of CxON and CxOL were 72.2% and 18.8%, respectively, and the CxONOL selectivity was 91.0%. The amount of sodium carbonate consumed was 22.1 g and the amount of sodium hydroxide consumed was 6.5 g, while the amount of sodium carbonate recovered was 27.7 g.

Example 4

The operation was carried out in the same manner as in [Example 3] except that a mixed alkaline aqueous solution composed of 23 parts by weight of 10 wt % sodium hydroxide aqueous solution and 77 parts by weight of 17 parts by weight sodium carbonate aqueous solution was used as the second alkaline solution, the feed amount of the second alkaline solution to the saponification step was changed to 0.67 g/min, and the first alkaline solution was covered by the recycling of the second waste alkali without addition of a new sodium carbonate aqueous solution. The pH of the first waste alkaline solution was 9.50, the CHP conversion was 3.6%, and the selectivities of CxON and CxOL were 52.0% and 26.2%, respectively. The pH of the second waste alkali after saponification was 13.38, the CHP conversion was 100%, the final selectivities of CxON and CxOL were 63.1% and 21.8%, respectively, and the CxONOL selectivity was 84.9%. The amount of sodium carbonate consumed was 41.9 g and the amount of sodium hydroxide consumed was 7.3 g, while the amount of sodium carbonate recovered was 46.5 g.

Comparative Example 2

The operation was carried out in the same manner as in [Example 4] except that the second alkaline solution was changed to only of 17 parts by weight of sodium carbonate aqueous solution without addition of sodium hydroxide aqueous solution.

The pH of the first waste alkaline solution was 9.45, the CHP conversion was 3.5%, and the selectivities of CxON and CxOL were 51.8% and 26.5%, respectively. The pH of the second waste alkaline solution after saponification was 12.03, the CHP conversion was 80.5%, the final selectivities of CxON and CxOL were 51.0% and 26.9%, respectively, and CxONOL selectivity was 77.9%. The amount of sodium carbonate consumed was 54.3 g, while the amount of sodium carbonate recovered was 48.9 g.

Example 5

The operation was carried out in the same manner as in [Example 3] except that the temperature of the neutralization step was set to 80° C., the temperature of the saponification step was set to 90° C., the 2630 ppm cobalt sulfate aqueous solution was mixed with the second alkaline aqueous solution at a rate of 1.36 mg/min (cobalt concentration was 10 ppm) and fed to the saponification step. The pH of the first waste alkaline solution was 9.40, the CHP conversion was 3.1%, and the selectivities of CxON and CxOL were 62.7% and 31.3%, respectively. The pH of the second waste alkali after saponification was 13.95, the CHP conversion was 100%, the final selectivities of CxON and CxOL were 74.7% and 21.2%, respectively, the CxONOL selectivity was 95.9%. The amount of sodium carbonate consumed was 22.1 g and the amount of sodium hydroxide consumed was 6.5 g while the amount of sodium carbonate recovered was 27.9 g.

The above results are summarized in Table 2 below.

TABLE 2

| | Neutralization step | | | | | | | Saponification step | |
|---|---|---|---|---|---|---|---|---|---|
| | Experimental conditions | | | Experimental results | | | | Experimental conditions | |
| | | | | | | | | 10% NaOH/ | |
| | Oxidation reaction feed g/min | First alkali solution feed g/min | Second waste alkali recycling | temperature °C. | First waste alkali solution pH | CHP conversion % | CxON selectivity % | CxOL selectivity % | 17% Na₂CO₃ mixing ratio wt/wt | Second alkali solution feed g/min |
| Ex. 1 | 20.1 | 0.36 | no | 120 | 9.57 | 4.3 | 51.7 | 25.8 | 100/0 | 0.136 |
| Ex. 2 | 20.1 | 0.36 | no | 120 | 9.57 | 4.3 | 51.7 | 25.8 | 100/0 | 0.107 |
| Com-Ex. 1 | — | — | — | — | — | — | — | — | 100/0 | 0.487 |
| Ex. 3 | 20.1 | 0.27 | all | 120 | 9.55 | 4.1 | 52.1 | 26.0 | 100/0 | 0.136 |
| Ex. 4 | 20.1 | 0 | all | 120 | 9.50 | 3.6 | 52.0 | 26.2 | 23/77 | 0.670 |
| Com-Ex. 2 | 20.1 | 0 | all | 120 | 9.45 | 3.5 | 51.8 | 26.9 | 0/100 | 0.670 |
| Ex. 5 | 20.1 | 0.27 | all | 80 | 9.40 | 3.1 | 62.7 | 31.3 | 100/0 | 0.136 |

TABLE 2-continued

| | Saponification step | | | | | | | Alkali balance | | |
|---|---|---|---|---|---|---|---|---|---|---|
| | Experimental conditions | | Experimental results Second waste alkaline solution pH | Neutralization/Saponification step Reaction results | | | | Consumed amount | | Recovered amount |
| | CoCO$_4$ addition | temperature °C. | | CHP conversion % | CxON selectivity % | CxOL selectivity % | CxONOL selectivity % | sodium carbonate g | sodium hydroxide g | sodium carbonate g |
| Ex. 1 | no | 140 | 13.89 | 100 | 71.9 | 18.5 | 90.4 | 29.4 | 6.5 | 32.3 |
| Ex. 2 | no | 140 | 13.37 | 100 | 63.5 | 20.4 | 83.9 | 29.4 | 5.2 | 30.8 |
| Com-Ex. 1 | no | 140 | 12.32 | 80.7 | 52.1 | 26.8 | 78.9 | — | 23.4 | 26.3 |
| Ex. 3 | no | 140 | 13.88 | 100 | 72.2 | 18.8 | 91.0 | 22.1 | 6.5 | 27.7 |
| Ex. 4 | no | 140 | 13.38 | 100 | 63.1 | 21.8 | 84.9 | 41.9 | 7.3 | 46.5 |
| Com-Ex. 2 | no | 140 | 12.03 | 80.5 | 51.0 | 26.9 | 77.9 | 54.3 | — | 48.9 |
| Ex. 5 | 2630 ppm: 1.36 mg/min | 90 | 13.95 | 100 | 74.7 | 21.2 | 95.9 | 22.1 | 6.5 | 27.9 |

Ex. = Example
Com-Ex. = Comparative Example

As can be seen from the above results, by making the pH of the second water phase (the second waste alkaline solution) in the saponification step higher than the pH of the first water phase (the first waste alkaline solution) in the neutralization step, particularly by making it higher than the pKa of hydroperoxide, it was possible to improve selectivity of ketone and/or alcohol and to reduce alkali consumption.

The invention claimed is:

1. A method for producing a ketone and/or alcohol by decomposing a hydroperoxide and an ester compound in an oxidation reaction solution obtained from oxidizing a hydrocarbon compound with molecular oxygen, in which the ketone and/or alcohol has the same number of carbon atoms as the hydrocarbon compound; wherein the method comprises:

neutralizing at least a part of a carboxylic acid in the oxidation reaction solution by contacting the oxidation reaction solution with a first alkaline solution comprising a carbonate of an alkali metal, and separating the reaction mixture into a first oil phase and a first water phase, wherein a content of the hydroperoxide in the first oil phase is more than 90% of a content of the hydroperoxide in the oxidation reaction solution, and a pH of the first water phase is 8.5 or more and 9.55 or less;

decomposing the hydroperoxide and the ester compound in the first oil phase by contacting the first oil phase with a second alkaline solution having a higher pH value than the first alkaline solution, and separating the reaction mixture into a second oil phase and a second water phase, wherein a pH of the second water phase is greater than or equal to the pKa of the hydroperoxide and 14.0 or less;

recovering at least a part of an unreacted hydrocarbon from the second oil phase;

obtaining the ketone and/or alcohol from the second oil phase after recovering at least a part of the unreacted hydrocarbon by purification;

recycling a part or all of the second water phase as a part of the first alkaline solution; and recovering the carbonate of an alkali metal from the first water phase and recycling the carbonate of an alkali metal to the first alkaline solution.

2. The method according to claim 1, wherein the pH of the second water phase is 12.6 or more and 14.0 or less.

3. The method according to claim 1, wherein the pH of the second water phase is 13.0 or more and 14.0 or less.

4. The method according to claim 1, further comprising recycling a part or all of the second water phase as a part of the second alkaline solution.

5. The method according to claim 1, wherein a transition metal compound is added to the second alkaline solution.

6. The method according to claim 1, wherein the hydrocarbon compound is cyclohexane, the hydroperoxide is cyclohexyl hydroperoxide, the ketone is cyclohexanone, and the alcohol is cyclohexanol.

7. A system for producing a ketone and/or alcohol by decomposing a hydroperoxide and an ester compound in an oxidation reaction solution obtained from oxidizing the hydrocarbon compound with molecular oxygen, in which the ketone and/or alcohol has the same number of carbon atoms as the hydrocarbon compound; wherein the system comprises:

a neutralization unit for neutralizing at least a part of a carboxylic acid in the oxidation reaction solution by contacting the oxidation reaction solution with a first alkaline solution comprising a carbonate of an alkali metal, and separating the reaction mixture into a first oil phase and a first water phase, wherein a content of the hydroperoxide in the first oil phase is more than 90% of a content of the hydroperoxide in the oxidation reaction solution, and a pH of the first water phase is 8.5 or more and 9.55 or less;

a saponification unit for decomposing the hydroperoxide and the ester compound in the first oil phase by contacting the first oil phase with a second alkaline solution having a higher pH value than the first alkaline solution, and separating the reaction mixture into a second oil phase and a second water phase, wherein a pH of the second water phase is greater than or equal to the pKa of the hydroperoxide and 14.0 or less;
an unreacted hydrocarbon recovery unit for recovering at least a part of an unreacted hydrocarbon from the second oil phase;
a purification unit for obtaining the ketone and/or alcohol from the second oil phase after recovering at least a part of the unreacted hydrocarbon by purification;
a recycling unit for recycling a part or all of the second water phase as a part of the first alkaline solution; and
an alkali recovery unit for recovering the carbonate of an alkali metal from the first water phase and recycling the carbonate of an alkali metal to the first alkaline solution.

* * * * *